United States Patent
Abe et al.

(10) Patent No.: US 10,966,862 B2
(45) Date of Patent: Apr. 6, 2021

(54) OPHTHALMIC LASER TREATMENT APPARATUS

(71) Applicant: NIDEK CO., LTD., Gamagori (JP)

(72) Inventors: Hitoshi Abe, Okazaki (JP); Seiki Tomita, Gamagori (JP); Masato Kawai, Okazaki (JP)

(73) Assignee: NIDEK CO., LTD., Gamagori (JP)

( * ) Notice: Subject to any disclaimer, the term of this patent is extended or adjusted under 35 U.S.C. 154(b) by 502 days.

(21) Appl. No.: 15/389,924

(22) Filed: Dec. 23, 2016

(65) Prior Publication Data

US 2017/0181889 A1 Jun. 29, 2017

(30) Foreign Application Priority Data

Dec. 29, 2015 (JP) ............................. JP2015-257577

(51) Int. Cl.
| A61F 9/008 | (2006.01) |
| A61B 18/04 | (2006.01) |
| A61B 18/00 | (2006.01) |

(52) U.S. Cl.
CPC ............ *A61F 9/008* (2013.01); *A61B 18/042* (2013.01); *A61B 2018/00988* (2013.01); *A61F 2009/0087* (2013.01); *A61F 2009/00887* (2013.01); *A61F 2009/00897* (2013.01)

(58) Field of Classification Search
None
See application file for complete search history.

(56) References Cited

U.S. PATENT DOCUMENTS

| 7,393,349 B2 * | 7/2008 | Abe ..................... A61B 3/0083 606/10 |
| 8,764,737 B2 * | 7/2014 | Kurtz .................. A61F 9/00825 606/4 |
| 2008/0319428 A1 * | 12/2008 | Wiechmann ............ A61F 9/008 606/5 |

FOREIGN PATENT DOCUMENTS

| JP | H03-118060 A | 5/1991 |
| JP | 2015-084965 A | 5/2015 |
| WO | 2011/085274 A1 | 7/2011 |

* cited by examiner

*Primary Examiner* — Jennifer Pitrak McDonald
*Assistant Examiner* — Elizabeth K So
(74) *Attorney, Agent, or Firm* — Oliff PLC

(57) ABSTRACT

An ophthalmic laser treatment apparatus for generating plasma by focusing a treatment laser beam to treat a treatment target portion of a patient's eye with the plasma includes: an irradiation optical system configured to irradiate the treatment laser beam to the patient's eye; a position adjusting unit configured to adjust a focusing position of the treatment laser beam in an optical axis direction with respect to a predetermined focusing reference position; an energy adjusting unit configured to adjust irradiation energy of the treatment laser beam; a storage unit configured to store evaluation information to evaluate a permissible combination of the focusing position and the irradiation energy with respect to the focusing position; and an evaluation unit configured to evaluate a combination of the focusing position adjusted by the position adjusting unit and the irradiation energy adjusted by the energy adjusting unit based on the evaluation information.

12 Claims, 7 Drawing Sheets

OPHTHALMIC LASER TREATMENT APPARATUS

CROSS-REFERENCE TO RELATED APPLICATIONS

This application is based upon and claims the benefit of priority from the prior Japanese Patent Applications No. 2015-257577 filed on Dec. 29, 2015, the entire contents of which are incorporated herein by reference.

BACKGROUND

This disclosure relates to an ophthalmic laser treatment apparatus for irradiating a patient's eye with a laser beam to treat the patient's eye.

There has been known an ophthalmic laser treatment apparatus for irradiating a patient's eye with a laser beam to that eye so that the irradiated laser beam generates plasma. For example, an ophthalmic laser treatment apparatus disclosed in Japanese unexamined patent application publication No. 3(1991)-118060 includes a convergent point position-adjusting optical system for setting a convergent point of a treatment laser beam at a position located more inside than the surface of an opaque body by a desired distance.

SUMMARY

Meanwhile, when an ophthalmic laser treatment apparatus configured to generate plasma to thereby treat a treatment target portion is to be used, a non-treatment target portion may exist near the treatment target portion. Further, the treatment target portion itself is different in strength with each person. Accordingly, a treatment for the treatment target portion may be performed by several times repeatedly changing irradiation energy of a treatment laser beam or a position of plasma generated by the treatment laser beam and irradiating the treatment laser beam. When a treatment condition is set for such a portion differing from patient to patient, e.g., in the strength of a treatment target portion, and subsequently a treatment for another patient is performed under the same condition without changing the previous condition, a non-treatment target portion of the current patient may be adversely affected.

The present disclosure has been made to address the above problems and has a purpose to provide an ophthalmic laser treatment apparatus configured to avoid irradiation of a treatment laser beam under an intended irradiation condition.

To achieve the above purpose, one aspect of the present disclosure provides an ophthalmic laser treatment apparatus for generating plasma by focusing a treatment laser beam to treat a treatment target portion of a patient's eye with the plasma, the apparatus comprising: an irradiation optical system configured to irradiate the treatment laser beam to the patient's eye; a position adjusting unit configured to adjust a focusing position of the treatment laser beam in an optical axis direction with respect to a predetermined focusing reference position; an energy adjusting unit configured to adjust irradiation energy of the treatment laser beam; a storage unit configured to store evaluation information to evaluate a permissible combination of the focusing position of the treatment laser beam and the irradiation energy with respect to the focusing position; and an evaluation unit configured to evaluate a combination of the focusing position adjusted by the position adjusting unit and the irradiation energy adjusted by the energy adjusting unit based on the evaluation information.

According to the present disclosure, an ophthalmic laser treatment apparatus capable of avoiding irradiation of a treatment laser beam under an intended irradiation condition can be provided.

DETAILED DESCRIPTION OF THE EXEMPLARY EMBODIMENTS

Figure 1:
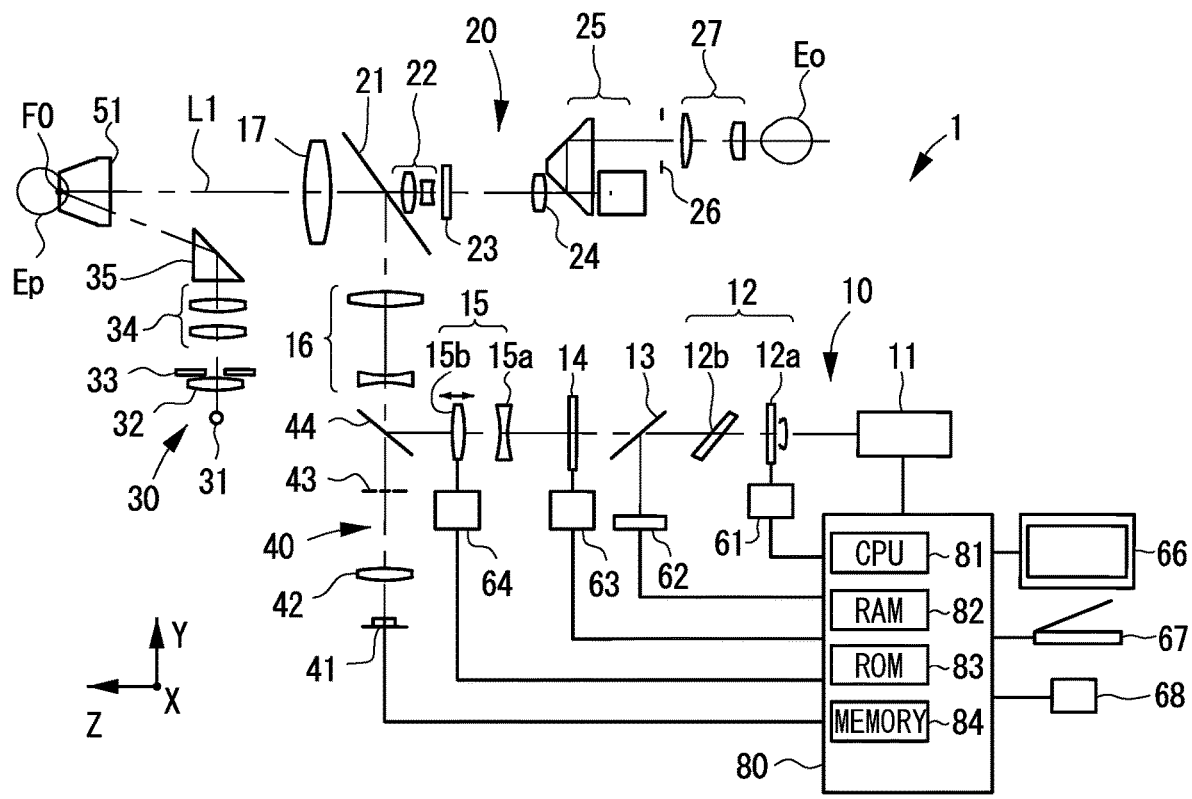
FIG. 1 is a schematic diagram of optical systems and a control system of an ophthalmic laser treatment apparatus in a present embodiment.

An embodiment which is one of typical embodiments of this disclosure will be explained below referring to the accompanying drawings. FIG. 1 is a schematic diagram of optical systems and a control system of an ophthalmic laser treatment apparatus 1 in the present embodiment. This ophthalmic laser treatment apparatus 1 in the present embodiment can be used in, for example, treatment for secondary cataract and others.

The ophthalmic laser treatment apparatus 1 in the present embodiment is provided with a laser irradiation optical system 10 and a controller 80. The ophthalmic laser treatment apparatus 1 in the present embodiment is further provided with an observation optical system 20, an illumination optical system 30, and an aiming optical system 40.

<Laser Irradiation Optical System>

The laser irradiation optical system 10 (an irradiation optical system) in the present embodiment is used to irradiate a laser beam for treatment (hereinafter referred to as a "treatment laser beam") to a patient's eye Ep. Specifically, the laser irradiation optical system 10 is configured to irradiate the treatment laser beam to a patient's eye Ep to thereby generate plasma in the vicinity of a focal (or focusing) position of the laser beam in the interior of the patient's eye Ep. Due to impact of this generated plasma, for example, a treatment target portion (tissues and others) of the patient's eye Ep is destroyed.

The laser irradiation optical system 10 in the present embodiment includes a laser source 11, an energy adjusting part 12, a shift adjusting part 15, an expander lens part 16, and an objective lens 17. The laser irradiation optical system 10 in the present embodiment is further provided with a beam splitter 13, a photodetector 62, a safety shutter 14, a dichroic mirror 44, and a dichroic mirror 21. The safety shutter 14 is connected to a shutter drive part 63.

The laser source 11 in the present embodiment is configured to emit a laser beam for treating a treatment target portion of the patient's eye Ep. The laser source 11 in the present embodiment is provided with a YAG (yttrium aluminum garnet) crystal doped with neodymium (Nd:YAG) as a laser rod: The laser source 11 in the present embodiment includes a Q-switch and thus can emit giant pulses. Specifically, the laser source 11 in the present embodiment is configured to emit an infrared laser beam (wavelength: 1064 nm). For example, a wavelength converting unit (a wavelength converting device or the like) may be placed in an optical path of the laser irradiation optical system 10 to convert an infrared laser beam (wavelength: 1064 nm) emitted from the laser source 11 to a visible laser beam (wavelength: 532 nm).

The energy adjusting part 12 (an energy adjusting unit) in the present embodiment is configured to adjust the energy of a treatment laser beam to be irradiated to tissues of the patient's eye Ep. Specifically, this energy adjusting part 12 in the present embodiment is configured to attenuate the energy of a laser beam emitted from the laser source 11. The energy adjusting part 12 in the present embodiment is provided with a ½ wave plate 12a and a polarizing plate 12b. This polarizing plate 12b is placed at a Brewster angle. The ½ wave plate 12a is connected to a drive part 61. This drive part 61 in the present embodiment includes a motor. The ½ wave plate 12a in the present embodiment is rotatable about an optical axis L1 of the treatment laser beam. The energy adjusting part 12 in the present embodiment can adjust the irradiation energy of the treatment laser beam in a range from 0.3 to 10 mJ.

The shift, adjusting part 15 (a position adjusting unit) in the present embodiment is used to displace a focusing position (i.e., a focal position or a convergent position) of the treatment laser beam in an optical axis. The shift adjusting part 15 in the present embodiment is provided with a concave lens 15a and a convex lens 15b. The convex lens 15b in the present embodiment is connected to a drive part 64. This drive part 64 in the present embodiment includes a motor. The convex lens 15b in the present embodiment is movable along the optical axis L1 of the treatment laser beam. The details of operations of the shift adjusting part 15 will be explained later.

The treatment laser beam emitted from the laser source 11 passes through the energy adjusting part 12, the beam splitter 13, the safety shutter 14, and the shift adjusting part 15 in sequence and then is reflected by the dichroic mirror 44. The treatment laser beam reflected by the dichroic mirror 44 passes through the expander lens part 16 and then is reflected by the dichroic mirror 21. The treatment laser beam reflected by the dichroic mirror 21 passes through the objective lens 17 and a contact lens 51 in sequence and is focused on the optical axis. The contact lens 51 is held in place by an operator.

The treatment laser beam emitted from the laser source 11 is expanded in beam diameter by the shift adjusting part 15 and the expander lens part 16 and enters as an almost parallel beam in the objective lens 17. In the present embodiment, the treatment laser beam passing through the objective lens 17 is focused on the optical axis L1 at a cone angle of about 16°.

<Aiming Optical System>

The aiming optical system 40 in the present embodiment will be described below. This aiming optical system 40 in the present embodiment is used to aim (guide) the treatment laser beam at a treatment target portion of the patient's eye Ep. The aiming optical system 40 in the present embodiment shares an optical path extending from the dichroic mirror 44 to the objective lens 17 with the laser irradiation optical system 10.

The aiming optical system 40 in the present embodiment includes an aiming light source 41, a collimator lens 42, and an aperture diaphragm 43. The aiming light source 41 in the present embodiment is configured to emit a visible laser beam having a wavelength of 635 nm. As the aiming light source 41, for example, any light sources, such as an LED or an SLD, may be used. The aperture diaphragm 43 in the present embodiment has two apertures. In the present embodiment, the dichroic mirror 44 makes the optical axis L1 of the treatment laser beam and the optical axis of the aiming beam coaxial with each other.

An aiming beam emitted from the aiming light source 41 falls on the aperture diaphragm 43 through the collimator lens 42. The aiming beam passing through the apertures of the aperture diaphragm 43 passes through the dichroic mirror 44 and the expander lens part 16 and then is reflected by the dichroic mirror 21. The aiming beam reflected by the dichroic mirror 21 passes through the objective lens 17 and the contact lens 51 in sequence and is focused or condensed at a focusing position (a focal position) on the optical axis L1. In the present embodiment, the aiming beam is collected at a position where an observation plane of the observation optical system 20 intersects with the optical axis L1. The aiming beam in the present embodiment is divided into two beams by the aperture diaphragm 43 and these divided beams converge into one beam at a focusing position beyond the objective lens 17. In the present embodiment, the position where the aiming beam is focused is assumed as a focusing reference position of the treatment laser beam.

<Focus Shift>

Figure 2:
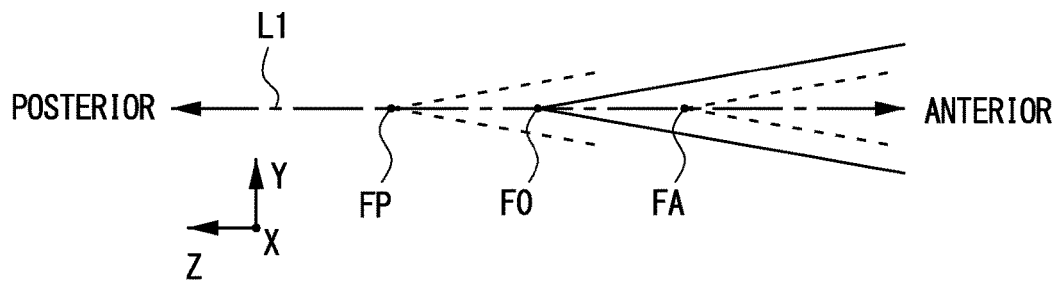
FIG. 2 is a diagram for focus shift.

A relationship between a focusing position (a focal position) of an aiming beam and a focusing position (a focal position) of a treatment laser beam will be described below in combination with FIG. 2. The aiming beam is focused at a predetermined position on the optical axis L1. In FIG. 2, the aiming beam is focused at a position F0 on the optical axis L1. In contrast, when the convex lens 15b is moved along the optical axis L1, the treatment laser beam in the present embodiment can be displaced (shifted) posteriorly or anteriorly with respect to the position F0 assumed as the focusing reference position on the optical axis L1.

In FIG. 2, a light flux of the treatment laser beam which is focused at the position F0 is indicated by a solid line. In FIG. 2, as one example, a light flux of the treatment laser beam which is focused at a position FP located on a more posterior side than the position F0 and a light flux of the treatment laser beam which is focused at a position FA located on a more anterior side than the position F0 are indicated by dotted lines. In the present embodiment, the "posterior side" indicates a position in a direction away from the objective lens 17 and the "anterior side" indicates a position in a direction toward the objective lens 17.

In the following description, shifting the focusing position (the focal position) of the treatment laser beam with respect to the focusing position (the focal position) of the aiming beam is also referred to as focus shift (a focus shift unit). Further, the focusing position of the treatment laser beam shifted by the focus shift is also referred to as a focus shift position. A shifted amount (a shifted distance) of the focusing position (the focal position) of the treatment laser beam with respect to the focusing position of the aiming beam is also referred to as a focus shift amount. The ophthalmic laser treatment apparatus 1 in the present embodiment can shift the focal position of the treatment laser beam in a range of +500 μm to −500 μm from the focal position (the position F0) of the aiming beam, <Illumination Optical System>

Returning to FIG. 1 the illumination optical system 30 in the present embodiment is explained. This illumination optical system 30 in the present embodiment is used to illuminate the patient's eye Ep. The illumination optical system 30 in the present embodiment is provided with a lamp 31, a lens 32, a diaphragm 33, a lens group 34 and a prism 35. The lamp 31 in the present embodiment emits visible light. For example, the lamp 31 may be a white light-emitting device or the like. Illumination light emitted from the lamp 31 passes through the lens 32, the diaphragm 33, and the lens group 34 in sequence and is reflected by the prism 35. The illumination light reflected by the prism 35 travels toward the patient's eye Ep. It is to be noted that slit light may be projected onto the patient's eye Ep by use of the diaphragm 33.

<Observation Optical System>

The observation optical system 20 in the present embodiment will be explained below. This optical system 20 in the present embodiment is used for an operator to observe the patient's eye Ep. The observation optical system 20 in the present embodiment shares the objective lens 17 and the dichroic mirror 21 with the irradiation optical system 10 and others. The observation optical system 20 in the present embodiment includes a magnification changing optical system 22, an operator protecting filter 23, an image forming lens 24, an erect prism group 25, a field diaphragm 2, and an eyepiece group 27. The field diaphragm 26 in the present embodiment is placed in a position optically conjugate with the position F0 (see FIG. 2 assumed as the reference position.

Observation light (e.g., illumination light reflected by the patient's eye Ep or aiming beam reflected by the patient's eye Ep) emitted from an observed portion passes through the objective lens 17, the dichroic mirror 21, the magnification changing optical system 22, the operator protecting filter 23, the image forming lens 24, and the erect prism group 25 in sequence and forms an intermediate image in a position of the field diaphragm 26. The observation light passing through an aperture of the field diaphragm 26 enters an operator's eye Eo through the eyepiece group 27. An observed image of the patient's eye Ep may be imaged by a camera.

<Controller>

The controller 80 in the present embodiment is explained below. The controller 80 in the present embodiment is a control unit configured to control operations of the ophthalmic laser treatment apparatus 1. The controller 80 in the present embodiment is provided with a CPU 81 (a processor), a RAM 82, a ROM 83, and a non-volatile memory 84. The CPU 81 in the present embodiment controls each part of the ophthalmic-laser treatment apparatus 1. The RAM 82 temporarily stores various information, for example. The ROM 83 stores for example various programs, defaults, and others. The non-volatile memory 84 is a non-transitory storage medium that can hold stored contents even if power supply is shut down. For instance, a USB memory detachably mounted in the controller 80, a flash ROM installed in the controller 80, and so on may be used as the non-volatile memory 84.

The controller 80 in the present embodiment is connected to the laser source 11, the drive part 61 (a first drive unit), the photodetector 62, the shutter drive part 63, the drive part 64 (a second drive unit), the aiming light source 41, the lamp 31, a monitor 66 (a display unit), a foot switch 67, and an operation switch 68. As an alternative, a hand switch may be used instead of the foot switch 67. The controller 80 in the present embodiment is a drive control unit, which can drive the drive part 61, the shutter drive part 63, the drive part 64, and others. The operation switch part 68 in the present embodiment is an operation input unit, which is used for adjustment of the irradiation energy, adjustment of the focus shift position, and other operations.

In the ophthalmic laser treatment apparatus 1 in the present embodiment, the ½ wave plate 12a is electrically driven (rotated). As an alternative, the ½ wave plate 12a may be manually driven (by an operators hand). For instance, a sensor may be connected to the ½ wave plate 12a so that the controller 80 detect a rotational position of the ½ wave plate 12a (i.e., an attenuated amount of a treatment laser beam by the energy adjusting part 12).

In the ophthalmic laser treatment apparatus 1 in the present embodiment, the convex lens 15 is electrically moved. As an alternative, the convex lens 15b may be manually moved (by an operator's hand). For instance, a sensor may be connected to the convex lens 15 so that the controller 80 detects a movement position of the convex lens 15b (i.e., a focus shift position).

The controller 80 in the present embodiment is a display control unit, which can control the contents to be displayed on the monitor 66. The monitor 66 in the present embodiment displays thereon an adjustment value of the irradiation energy, an adjustment value of the focus shift (a direction and a shift amount), and others. The ophthalmic laser treatment apparatus 1 in the present embodiment can adjust at least one of the irradiation energy and the focus shift position by operation of the operation switch part 68. For instance, an operator is allowed to change the adjustment value by operation of the operation switch part 68 while checking the adjustment value of the irradiation energy or the adjustment value of the focus shift position displayed on the monitor 66.

The foot switch 67 (an irradiation trigger unit) in the present embodiment is used to start irradiation of the treatment laser beam to the patient's eye Ep. The controller 80 in the present embodiment detects an output signal (an irradiation start signal) from the foot switch 67 and thus starts irradiation of the treatment laser beam to the patient's Ep. The controller 80 may be configured to automatically irradiate the treatment laser beam without use of the foot switch 67. Before irradiation of the treatment laser beam, the controller 80 in the present embodiment can detect the irradiation energy of the treatment laser beam to be irradiated to the patient's eye Ep by use of the safety shutter 14 and the photodetector 62.

In some cases, the monitor 66 in the present embodiment acts as a notification unit to display (notify) a warning. In other words, the controller 80 in the present embodiment serves as an notification control unit for controlling notification by the notification unit. Irrespective of the presence or absence of the warning display on the monitor serving as the display unit, for example, the ophthalmic laser treatment apparatus 1 may be provided with a buzzer and the controller 80 generates a warning sound.

<Operations of the Apparatus>

One example of the operations of the ophthalmic laser treatment apparatus 1 in the present embodiment will be described below with reference to FIG. 3. The ophthalmic laser treatment apparatus 1 in the present embodiment includes a plurality of irradiation modes of a treatment laser beam. Specifically the ophthalmic laser treatment apparatus 1 in the present embodiment is configured to operate in a first irradiation mode and a second irradiation mode. The controller 80 performs different controls between the first irradiation mode and the second irradiation mode in the present embodiment. The ophthalmic laser treatment apparatus in the present embodiment further includes a mode switching unit for switching between the first irradiation mode and the second irradiation mode.

The following description is predicated on that the first irradiation mode is automatically set at the time of initialization (step S101) of the ophthalmic laser treatment apparatus 1. The first irradiation mode in the present embodiment is suitably used in treatment for a patient's eye having a non-treatment target portion located on a near side of (i.e. on a more anterior position than) a treatment target portion. The second irradiation mode is suitably used in treatment for a patient's eye having a non-treatment target portion located on the far side of (i.e. on a more posterior position than) a treatment target portion.

When the ophthalmic laser treatment apparatus 1 is powered on, the controller 80 executes initialization of the ophthalmic laser treatment apparatus 1 in step S101. In step S101, the irradiation energy (the rotational position of the ½ wave plate 12a) and the focus shift position (the position of the convex lens 15b on the optical axis L1) are initialized. The processing contents to be executed by the controller 80 in step S101 will be explained later.

Upon completion of step S101, the controller 80 goes to step S102. The aiming light source 41 may be turned on in advance before step S102. In step S102, the controller 80 detects whether an operation to change the irradiation energy or the focus shift position has been performed by an operator. Specifically, the controller 80 in the present embodiment detects whether this change operation is present or not based on an output signal of the operation switch part 68.

When the controller 80 detects the change operation for the irradiation energy or the focus shift position, the controller 80 advances to step S103. The controller 80 executes the processing in step S103 and then goes to step S104.

Figure 4:
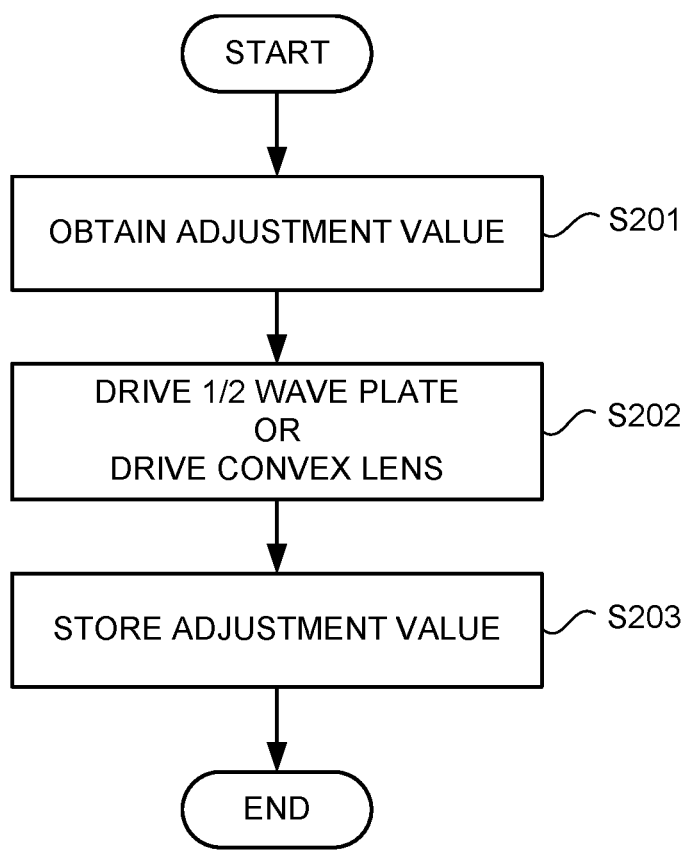
FIG. 4 is a flowchart for control of the ophthalmic laser treatment apparatus.

The control contents to be executed in step S103 by the controller 80 in the present embodiment will be explained below in combination with a flowchart of FIG. 4. In step S201, the controller 80 obtains an adjustment value (an intended change value) based on the output signal of the operation switch part 68 and others. In step S202, the controller 80 drives the ½ wave plate 12a so as to adjust the irradiation energy to the adjustment value obtained in step S201. In a case of changing the focus shift position, the controller 80 drives the convex lens 15b so as to adjust the focus shift position to the adjustment value obtained in step S201.

In step S203, successively, the controller 80 writes the adjustment value (data) obtained in step S201 in the non-volatile memory 84. The controller 80 in the present embodiment updates the adjustment value (data) stored in the non-volatile memory 84 every time the irradiation energy or the focus shift position is changed. At the time of initialization (step S101) at next power-on, the controller 80 in the present embodiment uses the adjustment value stored in step S203 in the non-volatile memory 84.

Figure 3:
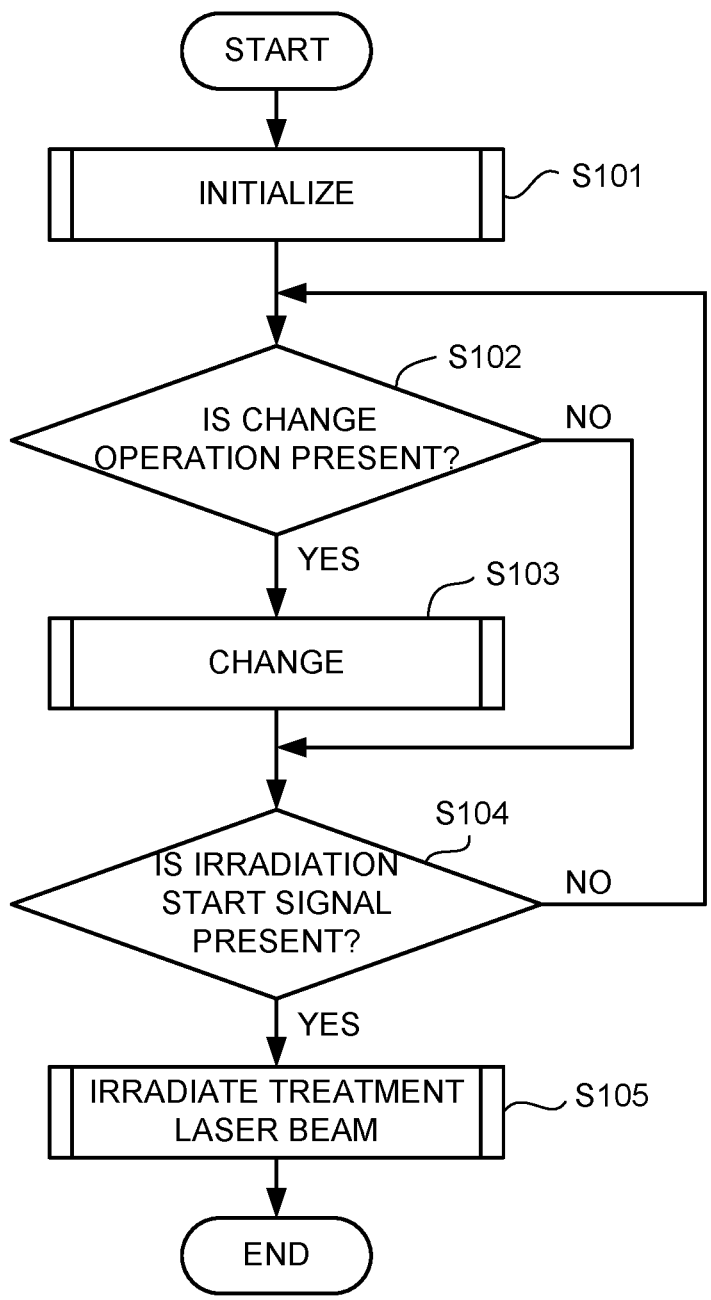
FIG. 3 is a flowchart for control of the ophthalmic laser treatment apparatus.

Returning to step S102 in FIG. 3, if the controller 80 detects no change operation for irradiation energy or focus shift position in step S102, the controller 80 advances to step S104. In other words, unless a change operation is performed by the operator, the controller 80 does not change, i.e., does maintain, the irradiation energy and the focus shift.

In step S104, the controller 80 detects whether a signal to start irradiation of a treatment laser beam has been generated. Specifically, the controller 80 in the present embodiment detects whether this irradiation start signal is present or not based on an output signal of the foot switch 67. If the irradiation start signal is detected in step S104, the controller 80 executes the processing in step S105. If the irradiation start signal is not detected in step S104, the controller 80 returns to step S102.

In step S105, the controller 80 retracts the safety shutter 14 from the optical axis L1 and then causes the laser source 11 to emit a laser beam (a treatment laser beam). As another configuration, the safety shutter 14 may be inserted and retracted by operation of the operation switch part 68 (i.e., by switching between a READY mode and a STANDBY mode). In this case, unless the safety shutter 14 is in a retreated position (the READY mode), emission of the laser beam is disabled even when the foot switch 67 is operated. The treatment laser beam to be irradiated from the ophthalmic laser treatment apparatus 1 is irradiated under the condition of the irradiation energy and the focus shift position adjusted before step S104.

<Evaluation of Combination>

Figure 5:
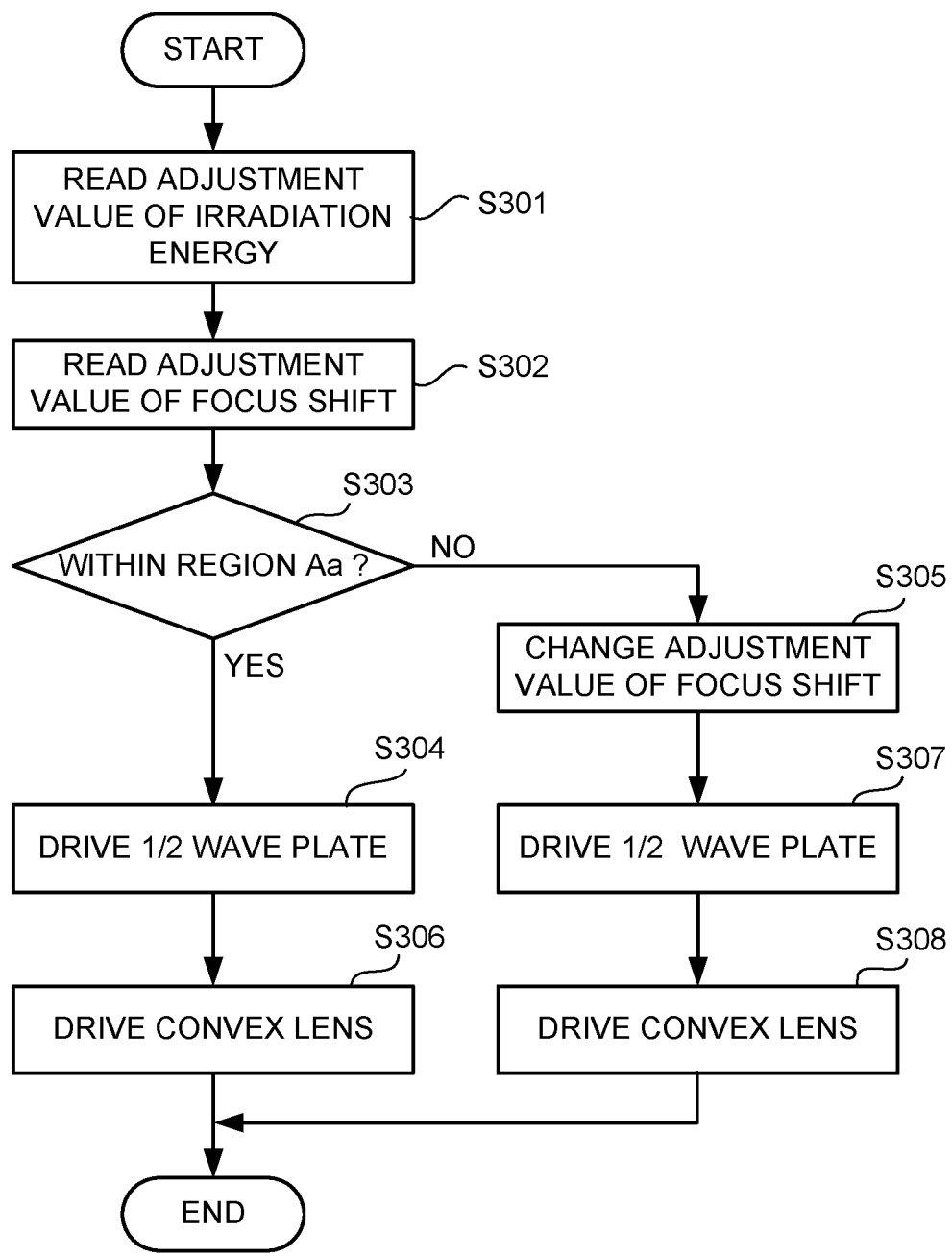
FIG. 5 is a flowchart for control of the ophthalmic laser treatment apparatus.
Figure 6:
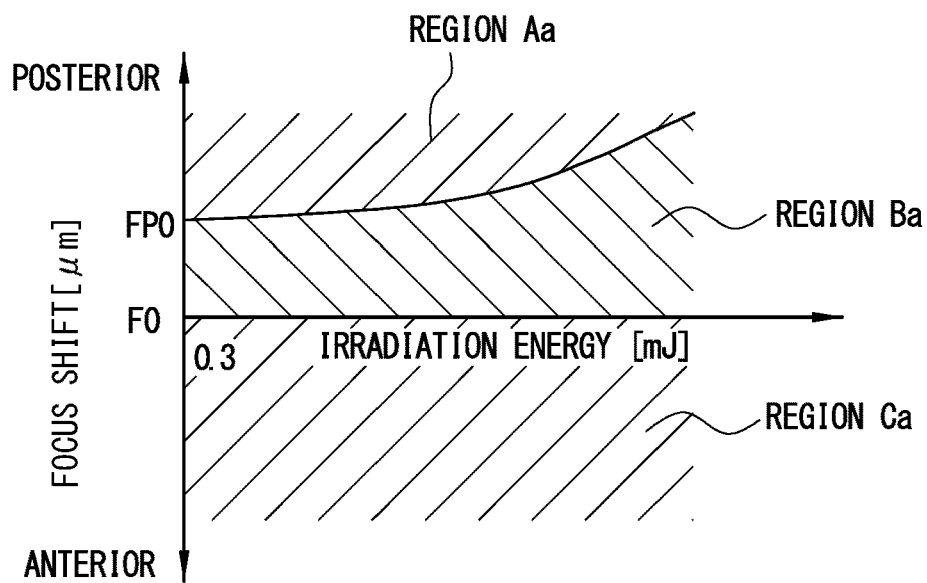
FIG. 6 is a graph for the control of the ophthalmic laser treatment apparatus.

A following explanation is given to combinations of the irradiation energy and the focus shift position with reference to a flowchart in FIG. 5 and a graph in FIG. 6. The ophthalmic laser treatment apparatus 1 in the present embodiment is provided with an evaluation unit for evaluating combinations of the irradiation energy and the focus shift position. The controller 80 in the present embodiment is an evaluation control unit configured to evaluate whether or not a combination of the irradiation energy and the focus shift position satisfies a predetermined condition.

In the present embodiment, as one example of evaluation, the irradiation energy is decided in consideration of the focus shift position. Alternatively, the focus shift position is decided in consideration of the irradiation energy. Specifically, the controller 80 in the present embodiment evaluates the combination of the irradiation energy and the focus shift position by considering the properties of plasma (a generation location, an impact range, etc.) generated by the treatment laser beam. Further, the controller 80 in the present embodiment evaluates the combination of the irradiation energy and the focus shift position by considering a positional relationship (an anterior-posterior direction) between a treatment target portion and a non-treatment target portion. The controller 80 in the present embodiment evaluates the combination of the irradiation energy and the focus shift position before starting irradiation of the treatment laser beam.

At the time when the initialization (step S101 in FIG. 3) of the ophthalmic laser treatment apparatus 1 is performed upon power-on of the apparatus main unit, the controller 80 in the present embodiment retrieves and evaluates a combination of the irradiation energy and the focus shift position having been set until just before previous power-off. The control contents to be executed in step S101 by the controller 80 will be explained below with reference to the flowchart in FIG. 4.

In step S301, the controller 80 reads a previously-set adjustment value of the irradiation energy (referred to as an intended adjustment value) from the non-volatile memory 84. In step S302, the controller 80 then reads a previously set adjustment value of the focus shift position (referred to as an intended adjustment value) from the non-volatile memory 84. In step S303, successively, the controller 80 evaluates (determines) whether or not the intended adjustment value of the irradiation energy read in step S301 and the intended adjustment value of the focus shift position read in step S302 satisfy predetermined conditions.

In the present embodiment, it is evaluated (determined) whether or not the intended adjustment value of the irradiation energy and the intended adjustment value of the focus shift position fall within a region Aa in the graph shown in FIG. 6. The region Aa in FIG. 6 indicates a range of combinations of values of irradiation energy and focus shift position which are regarded as not influencing a non-treatment target portion (i.e., a range of permissible combinations as a treatment condition) during a treatment to be performed with plasma on a treatment target portion having general (or average) strength. In contrast to the region Aa, regions Ba and Ca indicate cautionary ranges or impermissible ranges as a combination of treatment conditions.

If the intended adjustment value of the irradiation energy and the intended adjustment value of the focus shift position fall within the region Aa, the processing advances to step S304. In contrast, if those intended adjustment values fall outside the region Aa (i.e., fall within the region Ba or Ca), the processing goes to step S305. In the present embodiment, the properties shown in FIG. 6 are stored as table data in the non-volatile memory 84. In the present embodiment, evaluation information to be used for evaluation of combinations is stored as table data, but is not limited thereto. It is conceivable to store evaluation information using a predetermined calculation expression and others, not table data, into a memory and utilize it for exaltation. Further, it may be evaluated whether or not a combination of an intended adjustment value of the irradiation energy and an intended adjustment value of the focus shift position corresponds to a predetermined combination. (i.e., one specified combination). As an alternative, the evaluation information may be changed by operation of the operation switch part 68 or the like. In the present embodiment, the non-volatile memory 84 is used as a storage unit that stores table data. As a matter of course, another storage member (e.g., the ROM 83) may be used to store the table data.

Figure 7:
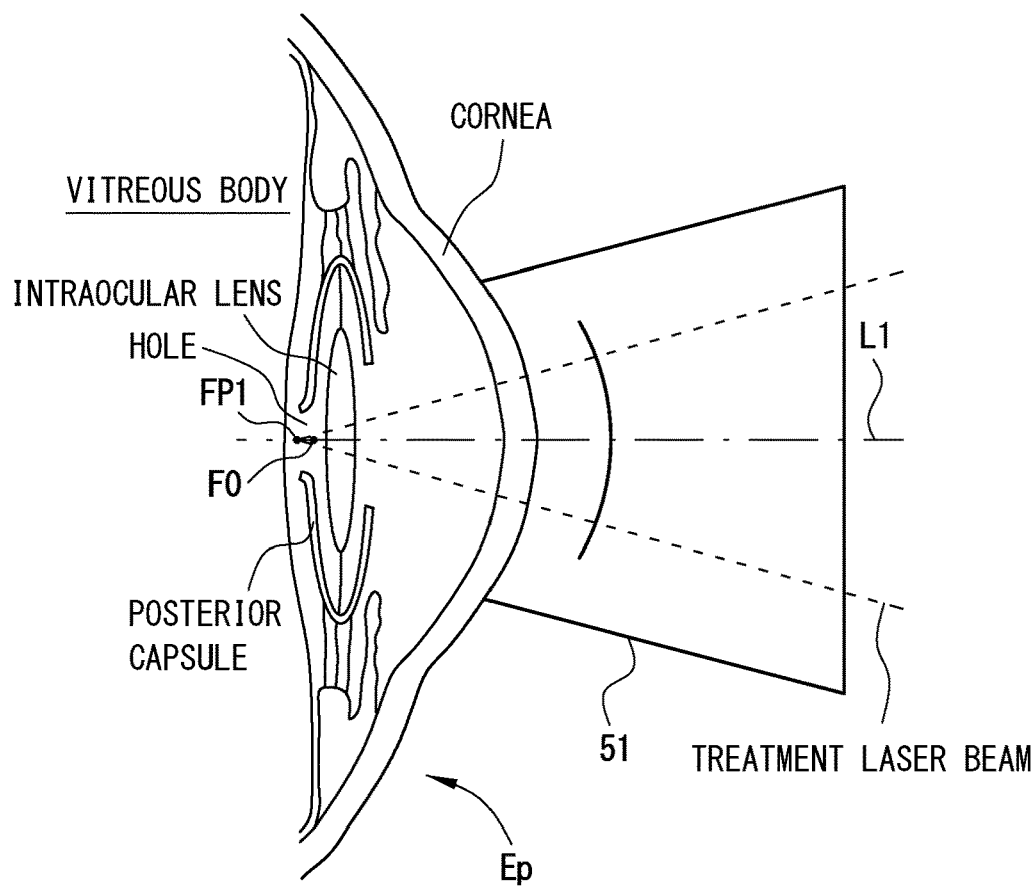
FIG. 7 is a diagram for treatment for a treated portion.

Herein, the background of the evaluation to be executed by the controller 80 in the present embodiment will be described below. A relationship between a treatment target portion and a non-treatment target portion is first explained with reference to FIG. 7 and then a relationship between irradiation energy and plasma is explained with reference to FIG. 8. FIG. 7 shows one example of the treatment using the first irradiation mode for a treatment target portion of a patient's eye Ep, showing a state where a posterior capsule (a treatment target portion) of the patient's eye Ep is formed with a hole by irradiation of a treatment laser beam. In front of the posterior capsule (the treatment target portion), an intraocular lens (a not target portion) is located. Explanations of the parts assigned with the same reference signs as those in other figures are omitted.

In FIG. 7, an aiming beam is focused at the position F0 and a treatment laser beam is focused at a position FP1 located on a more posterior side than the position F0. That is, by use of the focus shift, the focusing position of the treatment laser beam is shifted with respect to the focusing position of the aiming beam. Accordingly, a hole is formed in a posterior capsule (a treatment target portion) by impact of plasma, while the impact of plasma on the intraocular lens (the non-treatment target portion) is reduced, in case large impact of plasma transfers to the intraocular lens, a pit (a point-like dent or scratch) may be generated in the intraocular lens.

Figure 8:
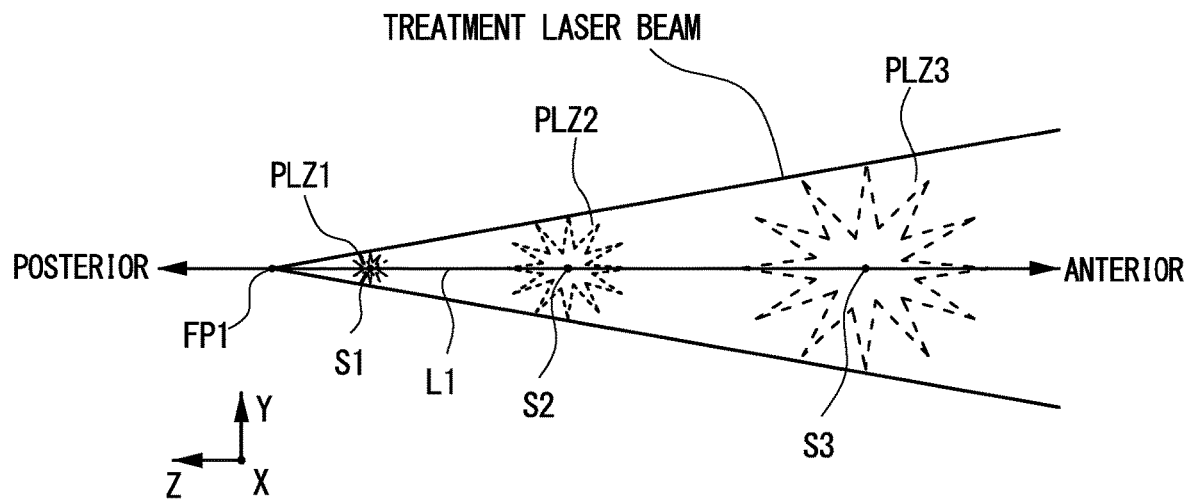
FIG. 8 is a diagram for a relationship between irradiation energy and plasma.

FIG. 8 is an explanatory view showing a relationship between irradiation energy and plasma of the treatment laser beam in the present embodiment. In FIG. 8, the treatment laser beam comes to focus at the position FP1, during which plasma occurs as indicated by reference signs PLZ1 to PLZ3 in FIG. 8. Specifically, the reference signs PLZ1 to PLZ3 indicate plasma generated by the treatment laser beam with the irradiation energy changed to different levels. To be specific, the plasma PLZ1 corresponds to a "low" level of irradiation energy, the plasma PLZ2 corresponds to a "middle" level of irradiation energy, and the plasma PLZ3 corresponds to a "high" level of irradiation energy. Positions S1 to S3 represent a center position of each generated plasma.

When the ophthalmic laser treatment apparatus 1 in the present embodiment is operated to change the irradiation energy of the treatment laser beam, the properties of plasma to be generated by the treatment laser beam are changed. In the present embodiment, specifically, as the irradiation energy is set higher, the center position of generated plasma gets located at a more anterior position. Changes in the center position of generated plasma depend on for example changes in energy density of the treatment laser beam. In the ophthalmic laser treatment apparatus 1 in the present embodiment, increasing the irradiation energy widens a plasma impact range. In other words, even when the focusing position of the treatment laser beam is shifted to the posterior side with respect to the focusing position of the aiming beam by use of the focus shift, the plasma impact range comes to the more anterior position as the irradiation energy of the treatment laser beam is set higher.

Returning to step S303 (see FIG. 5), the explanation is continued. The determination in step S303 executed by the controller 80 is performed in consideration of a situation and others explained referring to FIGS. 7 and 8. To be specific, in step S303, the controller 80 makes evaluation in view of the influence of plasma on a non treatment target portion. When a combination of an intended adjustment value of the irradiation energy and an intended adjustment value of the focus shift position falls within the region Aa (see FIG. 6), the controller 80 in the present embodiment judges that the plasma less influences the non-treatment target portion. When the combination of the intended adjustment values falls outside the region Aa, the controller 80 judges that the plasma greatly influences the non-treatment target portion.

In step S304, the controller 80 drives the ½ wave plate 12a to adjust the irradiation energy to the intended adjustment value read in step S301. In step S306, successively, the controller 80 drives the convex lens 15b to adjust the focus shift position to the intended adjustment value read in step S302. Specifically, the combination of the intended adjustment value of the irradiation energy read in step S301 and the intended adjustment value of the focus shift position read in step S302 falls within the region Aa (see FIG. 6), the controller 80 in the present embodiment drives either the ½ wave plate 12a or the convex lens 15b while directly using the adjustment value stored in the non-volatile memory 84.

Another control routine branching from step S303 will be explained below, in step S305, the controller 80 changes the intended adjustment value of the irradiation energy and the intended adjustment value of the focus shift position so that the combination of the intended adjustment value of the irradiation energy and the intended adjustment value of the focus shift position fails within the region Aa. The controller 80 in the present embodiment maintains the intended adjustment value of the irradiation energy and changes only the intended adjustment value of the focus shift position. To be specific, the controller 80 in the present embodiment maintains the intended adjustment value of the irradiation energy and changes the intended adjustment value of the focus shift position to an adjustment value falling within the region Aa closest to the region Ba. The controller 80 stores this changed adjustment value (intended adjustment value) in the non-volatile memory 84. In the present embodiment, the intended adjustment value of the irradiation energy is maintained and only the intended adjustment value of the us shift position is changed. As an alternative, it may be configured such that the intended adjustment value of the focus shift position is maintained and only the intended adjustment value of the irradiation energy is changed. As another alternative, both the intended adjustment value of the focus shift position and the intended adjustment value of the irradiation energy may be changed together.

In step S307, the controller 80 drives the ½ wave plate 12*a* to adjust the irradiation energy to the intended adjustment value read in step S301. Subsequently, in step S308, the controller 80 drives the convex lens 15*b* to adjust the focus shift position to the intended adjustment value changed in step S305.

In other words, when the intended adjustment value of the irradiation energy read in step S301 and the intended adjustment value of the focus shift position read in step S302 fall outside the region Aa (i.e., fall inside the region Ba or Ca), the controller 80 in the present embodiment changes the adjustment value (the intended adjustment value) stored in the non-volatile memory 84. Specifically, the controller 80 changes at least one of the intended adjustment value of the irradiation energy and the intended adjustment value of the focus shift position to bring the combination of the intended adjustment value of the irradiation energy and the intended adjustment value of the focus shift position into the region Aa.

As described above, the controller 80 in the present embodiment evaluates the combination of the irradiation energy and the focus shift position. Based on an evaluation result, the irradiation energy or the focus shift position is changed. This can avoid for example unintended irradiation of the treatment laser beam and, specifically, reduce a burden of the plasma impact on a non-treatment portion. Furthermore, for instance, the treatment for a treatment portion of a patient's eye Ep can be promptly performed.

First Modified Example

The above description is made on the operations of the ophthalmic laser treatment apparatus 1 using the first irradiation mode. As a first modified example of the control to be executed by the controller 80, operations of the ophthalmic laser treatment apparatus 1 using the second irradiation mode will be explained below. The ophthalmic laser treatment apparatus 1 in the present embodiment can be switched between the first irradiation mode and the second irradiation mode by operation of the operation switch part 68.

The second irradiation mode in the present embodiment is suitably used in treatment for a patient's eye having a non-treatment target portion located on a more posterior side than a treatment target portion. For instance, it is suitable to use the second irradiation mode to cut a pulling portion (a treatment target portion) of a vitreous body that pulls or tugs on a retina (a non-treatment target portion) by plasma generated by the ophthalmic laser treatment apparatus 1.

The following description is given mainly to different controls of the controller 80 between the first irradiation mode and the second irradiation mode. The first irradiation mode and the second irradiation mode in the present embodiment differ in the control to be executed at the time of initialization of the ophthalmic laser treatment apparatus 1 (see step S101 in FIG. 3). To be specific, the first irradiation mode and the second irradiation mode differ in table data (FIG. 6 for the first irradiation mode) to be used in step S303 and others (see FIG. 5).

Figure 9:
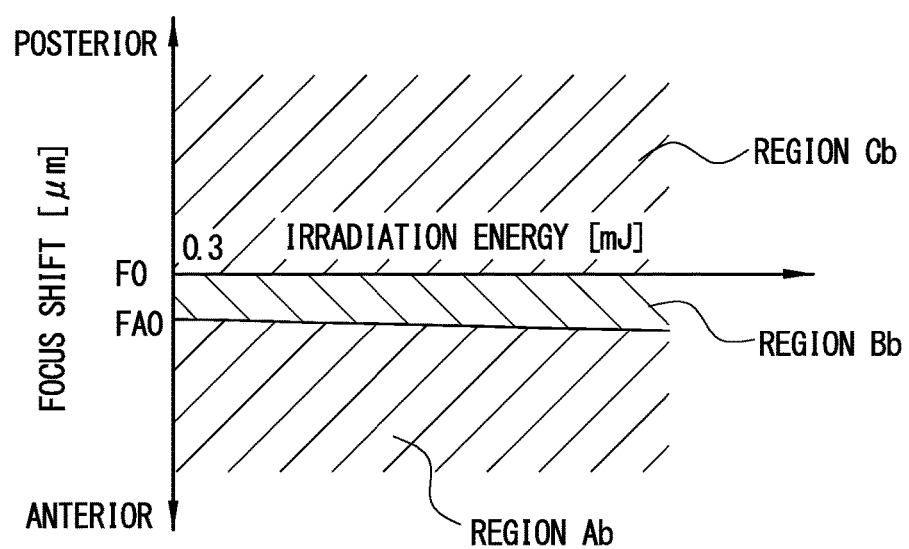
FIG. 9 is a graph for the control of the ophthalmic laser treatment apparatus.

Steps S303 and S305 in the second irradiation mode use table data of the properties shown in FIG. 9. In step S303 in the second irradiation mode, if the adjustment value of the irradiation energy the intended adjustment value) read in step S301 and the adjustment value of the focus shift position (the intended adjustment value) read in step S302 fall outside a region Ab (i.e., fall within a region Bb or Cb), the controller 80 changes the adjustment value having been stored in the non-volatile memory 84.

Specifically, in the second irradiation mode, as in the first irradiation mode, at least one of the intended adjustment value of the irradiation energy and the intended adjustment value of the focus shift position is changed so that a combination of the intended adjustment value of the irradiation energy and the intended adjustment value of the focus shift position falls within the region Ab. If the combination of the intended adjustment value of the irradiation energy and the intended adjustment value of the focus shift position is within the region Ab, the controller 80 drives the ½ wave plate 12*a* and the convex lens 15*b* without changing their intended adjustment values.

Comparing the table data (FIG. 6) in the first irradiation mode and the table data (FIG. 9) in the second irradiation mode, a boundary line between the region Aa and the region Ba in the table data of the first irradiation mode has a larger inclination angle (particularly, an angle formed between the boundary line and a straight line parallel to the axis of irradiation energy) than a boundary line between the region Ab and the region Bb in the table data of the second irradiation mode. Further, the inclination angle of the boundary line in the table data of the first irradiation mode is larger as the irradiation energy is higher.

The controller 80 in the second irradiation mode shifts the focusing position of a treatment laser beam to a near side of the focusing position of an aiming beam in order to reduce damage to a non-treatment target portion located more posteriorly than, i.e., on a far side of, a treatment target portion. Obviously, the irradiation energy of the treatment laser beam may be attenuated. The above-described control can cut a vitreous-body cord (a treatment target portion) that pulls a retina (a non-treatment target portion) by plasma impact, while reducing damage to the retina (the non-treatment target portion) due to the plasma impact.

Second Modified Example

Figure 10:
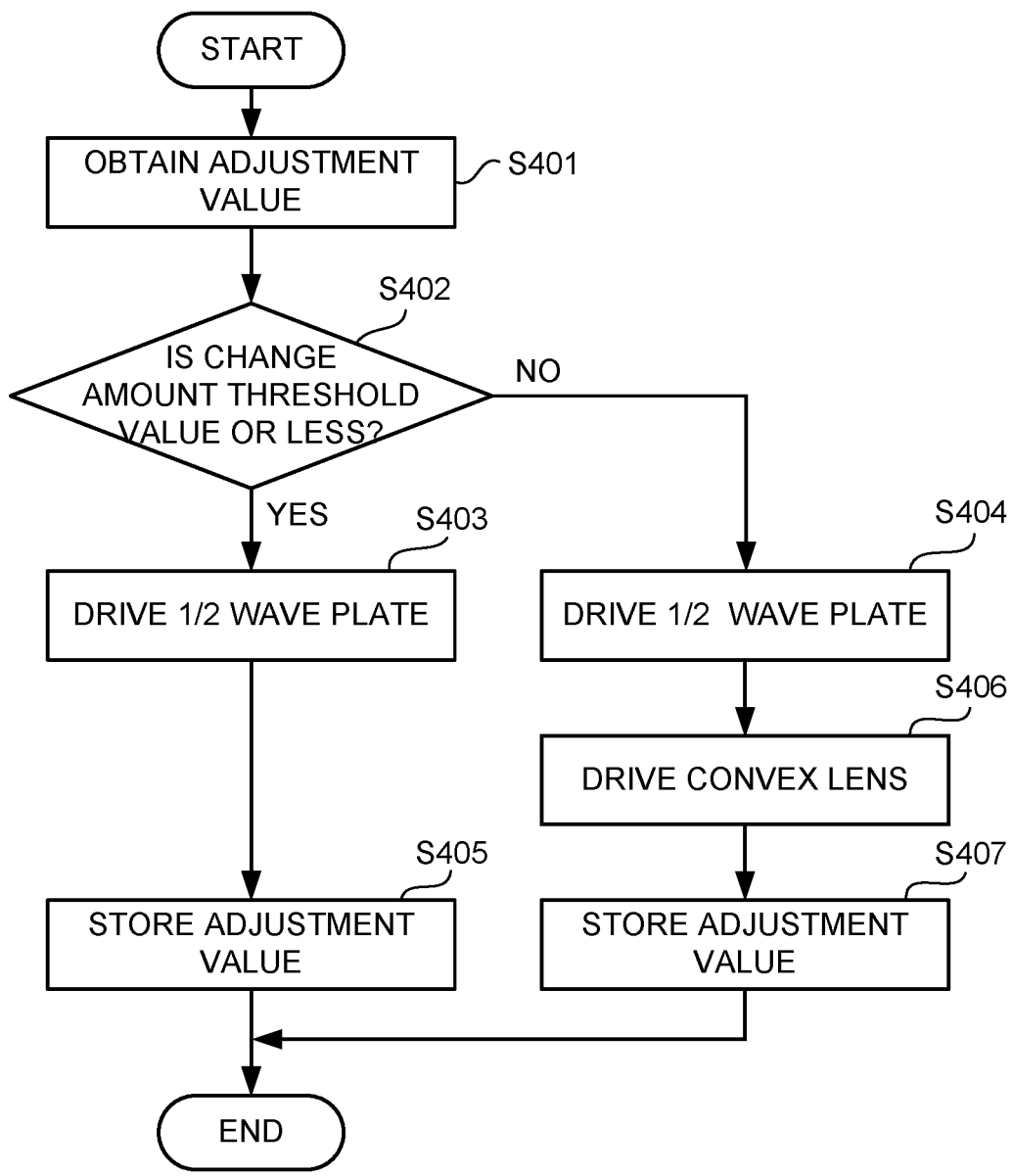
FIG. 10 is a flowchart for control of the ophthalmic laser treatment apparatus.

Another modified example (a second modified example) of the control to be executed by the controller 80 in step S103 will be described below. In step S103 in this modified example, the controller 80 executes a control flow shown in FIG. 10 instead of the control flow shown in FIG. 4. The control flow in FIG. 10 is configured to reduce excessive changes of the adjustment value (irradiation energy or focus shift position).

The controller 80 compares a current adjustment value and an intended change value and determines whether or not an intended change amount (an adjustment change amount) exceeds a predetermined threshold (step S402). When the intended change amount exceeds the threshold, the controller 80 corrects the intended change value (steps S404 and S406).

A control flow to be executed when the operation to change the irradiation energy is performed by an operator will be described below referring to FIG. 10. In step S401, an intended change value of the irradiation energy is obtained. The controller 80 has already read both an intended adjustment value of the irradiation energy and an intended adjustment value of the focus shift position. In step S402, subsequently, the controller 80 determines a relationship between an intended change amount of the irradiation energy and the threshold. If the intended change amount is equal to or less than the threshold, the controller 80 advances to step S403 in which the controller 80 drives the ½ wave plate 12*a* to adjust the irradiation energy to the adjustment value obtained in step S401, and goes to step S405. In step S405, the controller 80 stores the adjustment value used to drive the ½ wave plate 12*a*. In contrast, if the intended change amount exceeds the threshold, indicating that the irradiation energy was changed to a higher value, for example, the focus shift position is moved to the posterior side. To be concrete, the controller 80 drives the ½ wave plate 12*a* in step S404 so that the irradiation energy becomes the adjustment value obtained in step S401, and drives the convex lens 15*b* in step S406 so that the focus shift position is moved to the posterior side, and then goes to step S407.

In step S407, the controller 80 stores each adjustment value used to drive the ½ wave plate 12*a* and the convex lens 15*b*. Specifically, when the controller 80 advances from step S402 to step S403, indicating that the controller 80 has determined it is not necessary to correct the adjustment values (the irradiation energy and the focus shift position), the controller 80 only drives the ½ wave plate 12*a* (changes the irradiation energy).

In contrast, when the controller 80 advances from step S402 to step S404, indicating that the controller 80 has determined it is necessary to correct the adjustment values (the irradiation energy and the focus shift position), the controller 80 also drives the convex lens 15*b* (changes (corrects) the focus shift position) in addition to driving of the ½ wave plate 12*a* (changing of the irradiation energy).

For instance, if the adjustable range of irradiation energy is 0.3 to 10 mJ and the intended change amount of the irradiation energy exceeds 5 mJ (the threshold), the controller 80 also automatically changes the focus shift position in cooperation with changing of the irradiation energy. In the case of the first irradiation mode, the focus shift position may be automatically changed by use of the table data shown in FIG. 6. As a matter of course, if the change amount of the focus shift position is excessively large, the adjustment value (the irradiation energy or the focus shift position) may be corrected. Further, the adjustment value may also be corrected when the irradiation energy and the focus shift position are simultaneously changed.

The ophthalmic laser treatment apparatus 1 may be configured to execute only the control shown in FIG. 10. That is, the ophthalmic laser treatment apparatus 1 does not perform the control in FIG. 5. Moreover, for example, the above-described configuration may be applied only for adjustment of irradiation energy in the ophthalmic laser treatment apparatus. In other words, in a case where the ophthalmic laser treatment apparatus is not provided with the shift adjusting part 15 (the position adjusting unit), an intended excessively-high irradiation energy may be corrected or may be notified. It is to be noted that the above-described configuration may be applied to an ophthalmic laser treatment apparatus for treating a treatment target portion with a treatment laser beam without generating plasma.

Other conceivable options are provided as below. For instance, although the aforementioned embodiment corrects the irradiation energy or the focus shift position based on the evaluation result, the irradiation energy or the focus shift position remained unchanged may be notified to an operator. For instance, the controller 80 may display a warning on the monitor 66. If the ophthalmic laser treatment apparatus includes a beeper, the controller 80 may cause the beeper to sound a warning.

The aforementioned embodiment uses the aiming optical system 40 as an aiming unit for aiming a treatment laser beam. As an alternative, the observation optical system 20 may be configured to independently allow aiming of a treatment laser beam. For instance, even, in a configuration that the observation optical system includes a camera and aims a treatment laser beam by use of an output image of the camera, the aiming unit performs positioning using the aiming unit to the reference position (the position F0) and the position adjusting unit (the shift adjusting part 15) displaces the focusing position of the treatment laser beam with respect to the reference position.

The foregoing embodiments are mere examples and give no limitation to the present disclosure. The scope of this disclosure is shown by the claims, not in the aforementioned explanation, and may be embodied in other specific forms without departing from the claims and the equivalent signification and range thereto.

What is claimed is:

1. An ophthalmic laser treatment apparatus for generating plasma by focusing a treatment laser beam to treat a treatment target portion of a patient's eye with the plasma, the apparatus comprising:
    an irradiation optical system configured to irradiate the treatment laser beam to the patient's eye;
    an aiming optical system configured to irradiate an aiming beam to the patient's eye;
    a position adjusting unit comprising at least one lens and configured to adjust a focusing position of the treatment laser beam in an optical axis direction with respect to a predetermined reference position that is a focusing position of the aiming beam;
    an energy adjusting unit comprising a ½ wave plate and configured to adjust irradiation energy of the treatment laser beam by driving a motor to rotate the ½ wave plate;
    a memory configured to store evaluation information to evaluate a permissible combination of the focusing position of the treatment laser beam and the irradiation energy with respect to the focusing position of the treatment laser beam; and
    a processor configured to evaluate a combination of the focusing position of the treatment laser beam adjusted by the position adjusting unit and the irradiation energy adjusted by the energy adjusting unit based on the evaluation information, wherein
    the energy adjusting unit is configured to reduce, by driving the motor to rotate the ½ wave plate, the irradiation energy as the focusing position of the treatment laser beam approaches the predetermined reference position.

2. The ophthalmic laser treatment apparatus according to claim 1, wherein the processor is configured to evaluate the combination of the focusing position of the treatment laser beam and the irradiation energy before irradiation of the treatment laser beam.

3. The ophthalmic laser treatment apparatus according to claim 1, wherein the processor is configured to evaluate the combination of the focusing position of the treatment laser beam and the irradiation energy in consideration of an influence of the plasma on a non-treatment target portion.

4. The ophthalmic laser treatment apparatus according to claim 1, wherein the processor is configured to evaluate whether or not the combination of the focusing position of the treatment laser beam and the irradiation energy satisfies at least one predetermined condition.

5. The ophthalmic laser treatment apparatus according to claim 4, wherein the processor is configured to correct at least one of the focusing position of the treatment laser beam and the irradiation energy based on the evaluation result.

6. The ophthalmic laser treatment apparatus according to claim 4, further including a notification unit comprising at least one of a monitor and a buzzer and configured to provide notification of an evaluation result obtained by the processor.

7. The ophthalmic laser treatment apparatus according to claim 4, wherein
the at least one predetermined condition includes a first predetermined condition and a second predetermined condition,
the ophthalmic laser treatment apparatus is configured to operate in:
a first irradiation mode for irradiating the treatment laser beam under the first predetermined condition; and
a second irradiation mode for irradiating the treatment laser beam under the second predetermined condition, and
the apparatus further includes a mode switching unit configured to switch between the first irradiation mode and the second irradiation mode.

8. The ophthalmic laser treatment apparatus according to claim 7, wherein
the first predetermined condition is defined to reduce an influence of the plasma on a non-treatment target portion located on a near side of the treatment target portion, and
the second predetermined condition is defined to reduce the influence of the plasma on a non-treatment target portion located on a far side of the treatment target portion.

9. The ophthalmic laser treatment apparatus according to claim 1, wherein the processor is further configured to evaluate whether or not an adjustment change amount of at least one of the focusing position of the treatment laser beam and the irradiation energy exceeds a predetermined threshold.

10. The ophthalmic laser treatment apparatus according to claim 1, wherein the plasma is generated at a displaced position that is displaced from the predetermined reference position based on an adjustment result of the position adjusting unit.

11. The ophthalmic laser treatment apparatus according to claim 1, wherein the predetermined reference position and the focusing position of the treatment laser beam are configured to be adjusted independently from one another.

12. The ophthalmic laser treatment apparatus according to claim 1, wherein the irradiation optical system and the aiming optical system are respectively configured to irradiate the treatment laser beam and the aiming beam simultaneously.

* * * * *